US012773245B2

(12) United States Patent
Flint et al.

(10) Patent No.: US 12,773,245 B2
(45) **Date of Patent: *Oct. 27, 2026**

(54) SYSTEMS AND METHODS FOR BONE FIXATION ANCHOR, PLATE, AND SPACER DEVICES

(71) Applicant: GLOBUS MEDICAL, INC., Audubon, PA (US)

(72) Inventors: Brian Flint, Fort Washington, PA (US); Christina Tiongson, Norristown, PA (US); James Gault, Philadelphia, PA (US)

(73) Assignee: Globus Medical, Inc., Audubon, PA (US)

( * ) Notice: Subject to any disclaimer, the term of this patent is extended or adjusted under 35 U.S.C. 154(b) by 49 days.

This patent is subject to a terminal disclaimer.

(21) Appl. No.: 18/611,012

(22) Filed: Mar. 20, 2024

(65) Prior Publication Data

US 2024/0225705 A1 Jul. 11, 2024

Related U.S. Application Data

(63) Continuation of application No. 17/477,742, filed on Sep. 17, 2021, now Pat. No. 11,957,389, which is a (Continued)

(51) Int. Cl.

*A61B 17/80* (2006.01)
*A61B 17/17* (2006.01)

(Continued)

(52) U.S. Cl.

CPC ...... *A61B 17/8042* (2013.01); *A61B 17/1728* (2013.01); *A61B 17/7059* (2013.01); *A61B 17/8014* (2013.01); *A61B 17/8052* (2013.01); *A61B 17/8057* (2013.01); *A61B 17/8061* (2013.01); *A61B 17/86* (2013.01); *A61B 17/8605* (2013.01);

(Continued)

(58) Field of Classification Search

CPC . A61B 17/80; A61B 17/8042; A61B 17/8014; A61B 17/8052; A61B 17/8057; A61B 17/8061; A61B 17/17; A61B 17/1728; A61B 17/70; A61B 17/7059; A61B 17/86; A61B 17/8605

See application file for complete search history.

(56) References Cited

U.S. PATENT DOCUMENTS 1,105,105 A 7/1914 Sherman
2,486,303 A 10/1949 Longfellow (Continued)

FOREIGN PATENT DOCUMENTS

CN 201987653 U 9/2011
CN 202313691 U 7/2012

(Continued)

*Primary Examiner* — Christopher J Beccia

(57) ABSTRACT

Devices, systems, and methods of bone fixation. The bone fixation system includes a bone plate having an upper surface and a lower surface configured to be in contact with bone, the bone plate having a locking hole extending from the upper surface to the lower surface. The locking hole is configured to receive a locking fastener. The locking fastener has a threaded head portion configured to engage and lock to the bone plate.

18 Claims, 7 Drawing Sheets

Related U.S. Application Data continuation of application No. 16/122,995, filed on Sep. 6, 2018, now Pat. No. 11,147,599, which is a continuation-in-part of application No. 15/238,772, filed on Aug. 17, 2016, now Pat. No. 10,687,873.

(51) Int. Cl.
*A61B 17/70* (2006.01)
*A61B 17/86* (2006.01)
*A61B 17/00* (2006.01)

(52) U.S. Cl.
CPC . *A61B 2017/00858* (2013.01); *A61B 17/8047* (2013.01); *A61B 17/808* (2013.01); *A61B 17/809* (2013.01)

(56) References Cited

U.S. PATENT DOCUMENTS 3,716,050 A 2/1973 Johnston
4,493,317 A 1/1985 Klaue
4,524,765 A 6/1985 de Zbikowski
4,651,724 A 3/1987 Berentey et al.
4,683,878 A 8/1987 Carter
4,781,183 A 11/1988 Casey et al.
4,867,144 A 9/1989 Karas et al.
5,002,544 A 3/1991 Klaue et al.
5,041,114 A 8/1991 Chapman et al.
5,151,103 A 9/1992 Tepic et al.
5,259,398 A 11/1993 Vrespa
5,275,601 A 1/1994 Gogolewski et al.
5,364,399 A 11/1994 Lowery et al.
5,372,598 A 12/1994 Luhr et al.
5,423,826 A 6/1995 Coates et al.
5,601,553 A 2/1997 Trebing et al.
5,676,667 A 10/1997 Hausman
5,709,686 A 1/1998 Talos et al.
5,718,704 A 2/1998 Medoff
5,746,742 A 5/1998 Runciman et al.
5,785,712 A 7/1998 Runciman et al.
5,938,664 A 8/1999 Winquist et al.
6,001,099 A 12/1999 Huebner
6,096,040 A 8/2000 Esser
6,139,550 A * 10/2000 Michelson ............. A61B 17/80 606/295
6,152,927 A 11/2000 Farris et al.
6,206,881 B1 3/2001 Frigg et al.
6,283,969 B1 9/2001 Grusin et al.
6,309,393 B1 10/2001 Tepic et al.
6,322,562 B1 11/2001 Wolter
6,364,882 B1 4/2002 Orbay
6,533,786 B1 3/2003 Needham et al.
6,605,090 B1 8/2003 Trieu et al.
6,623,486 B1 9/2003 Weaver et al.
6,669,700 B1 12/2003 Farris et al.
6,669,701 B2 12/2003 Steiner et al.
6,712,820 B2 3/2004 Orbay
6,719,759 B2 4/2004 Wagner et al.
6,730,091 B1 5/2004 Pfefferle et al.
6,866,665 B2 3/2005 Orbay
6,955,677 B2 10/2005 Dahners
6,974,461 B1 12/2005 Wolter
7,001,387 B2 2/2006 Farris et al.
7,063,701 B2 6/2006 Michelson
7,128,744 B2 10/2006 Weaver et al.
7,137,987 B2 11/2006 Patterson et al.
7,153,309 B2 12/2006 Huebner et al.
7,179,260 B2 2/2007 Gerlach et al.
7,250,053 B2 7/2007 Orbay
7,294,130 B2 11/2007 Orbay
7,322,983 B2 1/2008 Harris
7,341,589 B2 3/2008 Weaver et al.
7,354,441 B2 4/2008 Frigg
7,604,657 B2 10/2009 Orbay et al.
7,632,277 B2 12/2009 Woll et al.
7,635,381 B2 12/2009 Orbay
7,637,928 B2 12/2009 Fernandez
7,655,029 B2 2/2010 Niedernberger et al.
7,682,379 B2 3/2010 Mathieu et al.
7,695,472 B2 4/2010 Young
7,695,502 B2 4/2010 Orbay et al.
7,722,653 B2 5/2010 Young et al.
7,740,648 B2 6/2010 Young et al.
7,776,076 B2 8/2010 Grady, Jr. et al.
7,857,838 B2 12/2010 Orbay
7,867,260 B2 1/2011 Meyer et al.
7,867,261 B2 1/2011 Sixto, Jr. et al.
7,875,062 B2 1/2011 Lindemann et al.
7,905,910 B2 3/2011 Gerlach et al.
7,909,858 B2 3/2011 Gerlach et al.
7,951,178 B2 5/2011 Jensen
7,951,179 B2 5/2011 Matityahu
7,976,570 B2 7/2011 Wagner et al.
D643,121 S 8/2011 Millford et al.
D646,785 S 10/2011 Milford
8,043,297 B2 10/2011 Grady, Jr. et al.
8,057,520 B2 11/2011 Ducharme et al.
8,062,296 B2 11/2011 Orbay et al.
8,100,953 B2 1/2012 White et al.
8,100,955 B2 * 1/2012 Blain ................ A61B 17/8042 606/291
8,105,367 B2 1/2012 Austin et al.
8,114,081 B2 2/2012 Kohut et al.
8,118,846 B2 2/2012 Leither et al.
8,162,950 B2 4/2012 Digeser et al.
8,167,918 B2 5/2012 Strnad et al.
8,177,820 B2 5/2012 Anapliotis et al.
8,246,661 B2 8/2012 Beutter et al.
8,252,032 B2 8/2012 White et al.
8,257,403 B2 9/2012 Den Hartog et al.
8,257,405 B2 9/2012 Haidukewych et al.
8,257,406 B2 9/2012 Kay et al.
8,262,707 B2 9/2012 Huebner et al.
8,267,972 B1 9/2012 Gehlert
8,317,842 B2 11/2012 Graham et al.
8,323,321 B2 12/2012 Gradl
8,337,535 B2 12/2012 White et al.
8,343,155 B2 1/2013 Fisher et al.
8,343,196 B2 1/2013 Schneider
8,382,807 B2 2/2013 Austin et al.
8,394,098 B2 3/2013 Orbay et al.
8,394,130 B2 3/2013 Orbay et al.
8,398,685 B2 3/2013 McGarity et al.
8,403,966 B2 3/2013 Ralph et al.
8,419,775 B2 4/2013 Orbay et al.
8,435,272 B2 5/2013 Dougherty et al.
8,439,918 B2 5/2013 Gelfand
8,444,679 B2 5/2013 Ralph et al.
8,491,593 B2 7/2013 Prien et al.
8,506,607 B2 8/2013 Eckhof et al.
8,506,608 B2 8/2013 Cerynik et al.
8,512,385 B2 8/2013 White et al.
8,518,090 B2 8/2013 Huebner et al.
8,523,862 B2 9/2013 Murashko, Jr.
8,523,919 B2 9/2013 Huebner et al.
8,523,921 B2 9/2013 Horan et al.
8,551,095 B2 10/2013 Fritzinger et al.
8,568,462 B2 10/2013 Sixto, Jr. et al.
8,574,268 B2 11/2013 Chan et al.
8,597,334 B2 12/2013 Mocanu
8,603,147 B2 12/2013 Sixto, Jr. et al.
8,617,224 B2 12/2013 Kozak et al.
8,632,574 B2 1/2014 Kortenbach et al.
8,641,741 B2 2/2014 Murashko, Jr.
8,641,744 B2 2/2014 Weaver et al.
8,663,224 B2 3/2014 Overes et al.
8,728,082 B2 5/2014 Fritzinger et al.
8,728,126 B2 5/2014 Steffen
8,740,905 B2 6/2014 Price et al.
8,747,442 B2 6/2014 Orbay et al.
8,764,751 B2 7/2014 Orbay et al.
8,764,808 B2 7/2014 Gonzalez-Hernandez
8,777,998 B2 7/2014 Daniels et al.
8,790,376 B2 7/2014 Fritzinger et al.

(56) References Cited

U.S. PATENT DOCUMENTS 8,790,377 B2 7/2014 Ralph et al.
8,808,333 B2 8/2014 Kuster et al.
8,808,334 B2 8/2014 Strnad et al.
8,834,532 B2 9/2014 Velikov et al.
8,834,537 B2 9/2014 Castanada et al.
8,852,246 B2 10/2014 Hansson
8,852,249 B2 10/2014 Ahrens et al.
8,864,802 B2 10/2014 Schwager et al.
8,870,931 B2 10/2014 Dahners et al.
8,888,825 B2 11/2014 Batsch et al.
8,906,076 B2 12/2014 Mocanu et al.
8,911,482 B2 12/2014 Lee et al.
8,926,675 B2 1/2015 Leung et al.
8,940,026 B2 1/2015 Hilse et al.
8,940,028 B2 1/2015 Austin et al.
8,940,029 B2 1/2015 Leung et al.
8,951,291 B2 2/2015 Impellizzeri
8,968,368 B2 3/2015 Tepic
9,011,457 B2 4/2015 Grady, Jr. et al.
9,023,052 B2 5/2015 Lietz et al.
9,050,151 B2 6/2015 Schilter
9,072,555 B2 7/2015 Michel
9,072,557 B2 7/2015 Fierlbeck et al.
9,103,367 B2 8/2015 Arnett
9,107,678 B2 8/2015 Murner et al.
9,107,711 B2 8/2015 Hainard
9,107,713 B2 8/2015 Horan et al.
9,107,718 B2 8/2015 Isch
9,113,970 B2 8/2015 Lewis et al.
9,149,310 B2 10/2015 Fritzinger et al.
9,155,577 B2 10/2015 Pfefferle et al.
9,161,791 B2 10/2015 Frigg
9,161,795 B2 10/2015 Chasbrummel et al.
9,168,075 B2 10/2015 Dell'Oca
9,179,950 B2 11/2015 Zajac et al.
9,179,956 B2 11/2015 Cerynik et al.
9,180,020 B2 11/2015 Gause et al.
9,211,151 B2 12/2015 Weaver et al.
9,259,217 B2 2/2016 Fritzinger et al.
9,259,255 B2 2/2016 Lewis et al.
9,271,769 B2 3/2016 Batsch et al.
9,283,010 B2 3/2016 Medoff et al.
9,295,506 B2 3/2016 Raven, III et al.
9,314,284 B2 4/2016 Chan et al.
9,320,554 B2 4/2016 Greenberg et al.
9,322,562 B2 4/2016 Takayama et al.
9,370,388 B2 6/2016 Globerman et al.
9,433,407 B2 9/2016 Fritzinger et al.
9,433,452 B2 9/2016 Weiner et al.
9,433,454 B2 9/2016 Paolino et al.
9,468,479 B2 10/2016 Marotta et al.
9,480,512 B2 11/2016 Orbay
9,486,262 B2 11/2016 Andermahr et al.
9,492,213 B2 11/2016 Orbay
9,510,878 B2 12/2016 Nanavati et al.
9,510,880 B2 12/2016 Terrill et al.
9,526,543 B2 12/2016 Castaneda et al.
9,545,277 B2 1/2017 Wolf et al.
9,566,097 B2 2/2017 Fierlbeck et al.
9,636,157 B2 5/2017 Medoff
9,649,141 B2 5/2017 Raven, III et al.
9,668,794 B2 6/2017 Kuster et al.
10,335,211 B2 7/2019 Chan et al.
11,147,599 B2 * 10/2021 Flint .................. A61B 17/1728
2002/0045901 A1 4/2002 Wagner et al.
2002/0156474 A1 10/2002 Wack et al.
2004/0097937 A1 5/2004 Pike et al.
2005/0107796 A1 5/2005 Gerlach et al.
2005/0131413 A1 6/2005 O'Driscoll et al.
2005/0187551 A1 8/2005 Orbay et al.
2005/0261688 A1 * 11/2005 Grady ................ A61B 17/8014 606/280
2006/0149265 A1 7/2006 James et al.
2006/0195104 A1 * 8/2006 Schlafli .............. A61B 17/8047 606/291
2006/0241607 A1 10/2006 Myerson et al.
2007/0270849 A1 11/2007 Orbay et al.
2008/0021477 A1 1/2008 Strnad et al.
2008/0234677 A1 * 9/2008 Dahners ............. A61B 17/8057 606/60
2008/0234749 A1 9/2008 Forstein
2008/0275510 A1 11/2008 Schonhardt et al.
2009/0024172 A1 1/2009 Pizzicara
2009/0024173 A1 1/2009 Reis, Jr.
2009/0118773 A1 5/2009 James et al.
2009/0198285 A1 8/2009 Raven, III
2009/0228010 A1 9/2009 Gonzalez-Hernandez et al.
2009/0228047 A1 9/2009 Derouet et al.
2009/0248084 A1 10/2009 Hintermann
2009/0281543 A1 11/2009 Orbay et al.
2009/0312760 A1 12/2009 Forstein et al.
2010/0057086 A1 3/2010 Price et al.
2010/0114097 A1 5/2010 Siravo et al.
2010/0121326 A1 5/2010 Woll et al.
2010/0274247 A1 10/2010 Grady, Jr. et al.
2011/0106086 A1 5/2011 Laird
2011/0218580 A1 9/2011 Schwager et al.
2012/0059424 A1 3/2012 Epperly et al.
2012/0323284 A1 12/2012 Baker et al.
2013/0018426 A1 1/2013 Tsai et al.
2013/0060291 A1 3/2013 Petersheim
2013/0096631 A1 4/2013 Leung et al.
2013/0123841 A1 5/2013 Lyon
2013/0138156 A1 5/2013 Derouet
2013/0150902 A1 6/2013 Leite
2013/0165981 A1 6/2013 Clasbrummet et al.
2013/0211463 A1 8/2013 Mizuno et al.
2013/0325071 A1 12/2013 Niemiec et al.
2014/0005728 A1 1/2014 Koay et al.
2014/0018862 A1 1/2014 Koay et al.
2014/0031879 A1 1/2014 Sixto, Jr. et al.
2014/0053696 A1 2/2014 Reed
2014/0094856 A1 4/2014 Sinha
2014/0121710 A1 5/2014 Weaver et al.
2014/0180345 A1 6/2014 Chan et al.
2014/0277178 A1 9/2014 O'Kane et al.
2014/0277181 A1 9/2014 Garlock
2014/0316473 A1 10/2014 Pfeffer
2014/0330320 A1 11/2014 Wolter
2014/0378975 A1 12/2014 Castaneda et al.
2015/0051650 A1 2/2015 Verstreken et al.
2015/0051651 A1 2/2015 Terrill et al.
2015/0073486 A1 3/2015 Marotta et al.
2015/0105829 A1 4/2015 Laird
2015/0112355 A1 4/2015 Dahners et al.
2015/0134011 A1 5/2015 Medoff
2015/0142065 A1 5/2015 Schonhardt et al.
2015/0190185 A1 7/2015 Koay et al.
2015/0209091 A1 7/2015 Sixto, Jr. et al.
2015/0216571 A1 * 8/2015 Impellizzeri ....... A61B 17/8033 264/279
2015/0223852 A1 8/2015 Lietz et al.
2015/0272638 A1 10/2015 Langford
2015/0282851 A1 10/2015 Michel
2015/0313653 A1 11/2015 Ponce et al.
2015/0313654 A1 11/2015 Horan et al.
2015/0327898 A1 11/2015 Martin
2015/0351816 A1 12/2015 Lewis et al.
2016/0022336 A1 1/2016 Bateman
2016/0030035 A1 2/2016 Zajac et al.
2016/0045237 A1 2/2016 Cerynik et al.
2016/0045238 A1 2/2016 Bohay et al.
2016/0074081 A1 3/2016 Weaver et al.
2016/0166297 A1 6/2016 Mighell et al.
2016/0166298 A1 6/2016 Mighell et al.
2016/0262814 A1 9/2016 Wainscott
2016/0278828 A1 9/2016 Ragghianti
2016/0310183 A1 10/2016 Shaw et al.
2016/0310185 A1 10/2016 Sixto et al.
2016/0324552 A1 11/2016 Baker et al.
2016/0354122 A1 12/2016 Montello et al.
2017/0035478 A1 2/2017 Andermahr et al.
2017/0042592 A1 2/2017 Kim
2017/0042596 A9 2/2017 Mighell et al.

(56) References Cited

U.S. PATENT DOCUMENTS

| | | | |
|---|---|---|---|
| 2017/0049493 A1 | 2/2017 | Gauneau et al. | |
| 2017/0065312 A1 | 3/2017 | Lauf et al. | |
| 2017/0202585 A1* | 7/2017 | Leak .................. | A61B 17/8042 |
| 2017/0215931 A1 | 8/2017 | Cremer et al. | |
| 2017/0238980 A1 | 8/2017 | Lauf et al. | |
| 2018/0049787 A1 | 2/2018 | Davison et al. | |

FOREIGN PATENT DOCUMENTS

| | | | |
|---|---|---|---|
| CN | 202821574 | U | 3/2013 |
| CN | 202821575 | U | 3/2013 |
| CN | 203506858 | U | 4/2014 |
| CN | 203815563 | U | 9/2014 |
| CN | 105982727 | A | 10/2016 |
| EP | 3348218 | A1 | 7/2018 |
| FR | 2846870 | A1 | 5/2004 |
| FR | 2928259 | A1 | 9/2009 |
| JP | 2003210478 | A | 7/2003 |
| JP | 2010-536427 | A | 12/2010 |
| JP | 2015-519144 | A | 7/2015 |
| JP | 2015526202 | A | 9/2015 |
| JP | 2018-110864 | A | 7/2018 |
| TW | 201316942 | A | 5/2013 |
| WO | 2011109127 | A1 | 9/2011 |
| WO | 2016079504 | A1 | 5/2016 |

* cited by examiner

SYSTEMS AND METHODS FOR BONE FIXATION ANCHOR, PLATE, AND SPACER DEVICES

CROSS-REFERENCE TO RELATED APPLICATIONS

This application is a continuation application of U.S. patent application Ser. No. 17/477,742 filed on Sep. 17, 2021 (published as U.S. Pat. Pub. No. 2022-0000526), which is a continuation application of U.S. patent application Ser. No. 16/122,995 filed on Sep. 6, 2018, now U.S. Pat. No. 11,147, 599, which is a continuation-in-part of U.S. patent application Ser. No. 15/238,772, filed on Aug. 17, 2016, now U.S. Pat. No. 10,687,873, each of which are incorporated by reference herein in its entirety for all purposes.

FIELD

The present invention relates to a bone fixation plate and fastener systems used to stabilize vertebrae and other bony anatomy. More specifically, the present invention relates to systems and methods for locking a fastener into a bone plate.

BACKGROUND

Bones and bony structures are susceptible to a variety of weaknesses that can affect their ability to provide support and structure. Weaknesses in bony structures may have many causes, including degenerative diseases, tumors, fractures, and dislocations. Advances in medicine and engineering have provided doctors with a plurality of devices and techniques for alleviating or curing these weaknesses.

In the field of orthopedic surgery, and more specifically spinal surgery, bone fasteners may be used for fixation or for the fastening of orthopedic devices or instruments to bone tissue. An exemplary use of bone fastener may include using the bone fastener to fasten an orthopedic device, such as a bone plate, a spinal spacer, and/or a combination thereof, to a vertebral body for the treatment of a deformity or defect in a patient's spine. Bone fasteners can be secured to a number of vertebral bodies and a bone plate can then be connected to the vertebral bodies via the bone fasteners to fuse a segment of the spine. In another example, bone fasteners can be used to fix the location of a spinal spacer once the spacer is implanted between adjacent vertebral bodies. In yet another example, bone fasteners can be fastened to a number of vertebral bodies to anchor a spinal rod in place along a spinal column to treat a spinal deformity.

In the case of severely weakened bone, surgeons may face challenges in finding proper purchase of the bone fastener into the bone and proper attachment to the bone plate. Therefore, to overcome disadvantages noted above, the present disclosure provides bone fixation systems and methods using bone fasteners with threaded heads to engage and deform a textured portion of a bone plate.

SUMMARY

To meet this and other needs, the present disclosure provides a bone fixation system having a bone plate and a locking fastener. The bone plate may include an upper surface and a lower surface that may be in contact with a bone. The bone plate may also include a locking hole extending from the upper surface to the lower surface, the locking hole may include a textured portion. The textured portion may include a texture that is a non-threaded surface. The locking fastener may include a head portion and a shaft portion and the locking fastener may be received by the locking hole and may be inserted into the bone. The head portion may be threaded and configured to engage the textured area of the locking hole.

The present disclosure also provides a bone fixation system including a spacer that may be inserted in between two adjacent vertebral bodies and a bone plate that may engage the spacer. The bone plate may have an upper surface and a lower surface that may be in contact with bone. The bone plate may further have a locking hole extending from the upper surface to the lower surface, the locking hole may include a textured portion and non-textured portion. The textured portion may include a texture that is a non-threaded surface. The bone fixation system may include a locking fastener that may be received in the locking hole and that may be inserted into the bone. The locking fastener may have a threaded head portion configured to lock to the bone plate. The threaded head portion may deform the textured portion of locking hole.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein.

DETAILED DESCRIPTION

Embodiments of the disclosure are generally directed to devices, systems, and methods for bone stabilization. Specifically, embodiments are directed to bone plating with locking and/or non-locking fasteners for engaging with a bone fastener. The hole designs may allow for fixed angle and/or variable angle fixation. Systems and methods disclosed herein may allow for locking bone screws into a spinal plate or integrated plate-spacer to create a rigid construct and prevent back-out of screws while maintaining a preferred screw trajectory using a spherical or conical screw head profile and with tapering dual-lead threads at a specified torque. Some embodiments further include locking fasteners with self-forming threads configured to displace the plate material, thereby locking the fastener to the plate.

The present disclosure relates to exemplary embodiments of locking screws into a plate or integrated plate spacer. This may be accomplished through interference/cross-threading of tapered dual-lead threads on a head of the locking screw engaging with a screw hole or socket with a series of helical sweeps, diamond knurls, or similar relief cuts arranged about the central axis of the screw hole or socket. Tightening of the dual-lead threads of the screw head into these relief cuts creates rigid fixation of the screw and prevents loosening and screw back-out. As an example, the material of the screw may be the same as the plate/integrated-plate spacer or a harder material to promote controlled deformation and rigid fixation. The helical sweeps, diamond knurls, or similar relief cuts may allow for both fixed and variable angle locking screws with conical variability up to 10 degrees.

The plate(s) and/or plate-spacer device(s) may be adapted to contact one or more vertebral bodies. The configuration of the locking screw and/or screw hole of the present disclosure may be used by various plates and plate-spacer devices known in the art. Such exemplary bone plates and plate-spacer devices have been described, for example, in U.S. Pat. Nos. 9,326,802; 9,095,387; 9,044,275; and 9,044,275 which are incorporated herein by reference in their entireties. For purposes of illustration, one exemplary bone fixation plate is described in FIG. 1.

Figure 1:
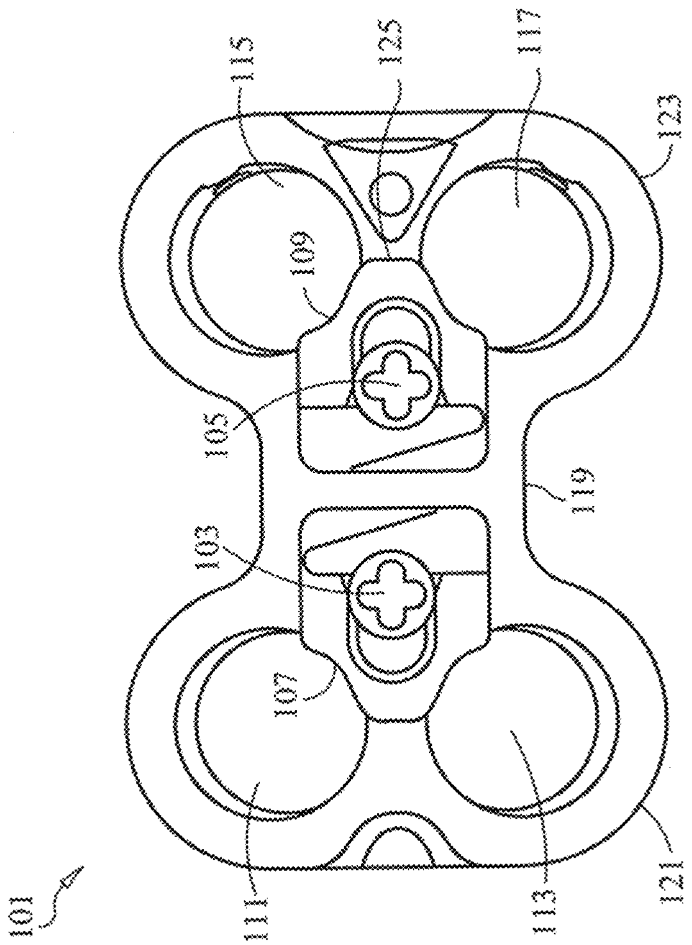
FIG. 1 illustrates an exemplary bone plate fixation device to used according to the principles of the present disclosure.

FIG. 1 shows one exemplary embodiment of a bone fixation plate 101 that may be used with the locking screw/screw hole configuration of the present disclosure. The plate may be secured to two vertebrae in order to maintain the vertebrae integrally with respect to one another in a desired orientation and at a desired spacing from one another. Plate 101 may include two fastening devices, such as screws 103-105 or the like, which are operatively communicable with plates 107-109. The plate also includes four openings 111-117, through which screws (not shown) may be used to fasten the plate 101 to the vertebrae.

Plate 101 and the screws may be comprised of any material, such as a metal, alloy, or any combination of the two. Preferably, the material used to construct the plate and the screws allows the plate 101 to maintain its structural integrity while allowing for a desired amount of resiliency. Furthermore, the material used is preferably bio-compatible and capable of withstanding the conditions of a body over a desired period of time. In some embodiments, this is achieved by manufacturing the plate 101 and screws using metals such as titanium or stainless steel. Titanium has sufficient ductility to permit a desired amount of curving of the plate 101 to conform to the shape of the vertebrae, yet has the strength to maintain its structural integrity.

In the exemplary embodiment of FIG. 1, bone fixation plate 101 comprises a center portion 119 and two distal portions 121-123. Each distal portion 121-123 may be attached to a different vertebra using fasteners, such as screws, that pass through openings 111-117.

Bone plates may be comprised of titanium, stainless steel, cobalt chrome, carbon composite, plastic or polymer—such as polyetheretherketone (PEEK), polyethylene, ultra-high molecular weight polyethylene (UHMWPE), resorbable polylactic acid (PLA), polyglycolic acid (PGA), combinations or alloys of such materials or any other appropriate material that has sufficient strength to be secured to and hold bone, while also having sufficient biocompatibility to be implanted into a body. Similarly, the fasteners may be comprised of titanium, cobalt chrome, cobalt-chrome-molybdenum, stainless steel, tungsten carbide, combinations or alloys of such materials or other appropriate biocompatible materials. Although the above list of materials includes many typical materials out of which bone plates and fasteners are made, it should be understood that bone plates and fasteners comprised of any appropriate material are contemplated.

Referring now to FIGS. 2-10, exemplary embodiments of the present disclosure are presented. With regards to FIGS. 2-6, one or more locking fasteners may be inserted into a plate or integrated plate spacer through interference/cross-threading of tapered dual-lead threads on the screw head with a screw hole or socket with a series of helical sweeps, diamond knurls, or similar relief cuts arranged about the central axis of the screw hole or socket. Tightening of the dual-lead threads of the screw head into these relief cuts creates rigid fixation of the screw and prevents loosening and screw back-out.

The material of the screw may be the same as the plate/integrated-plate spacer or a harder material to promote controlled deformation and rigid fixation. The helical sweeps, diamond knurls, or similar relief cuts allow for both fixed and variable angle locking screws with conical variability up to 10 degrees.

Figure 3:
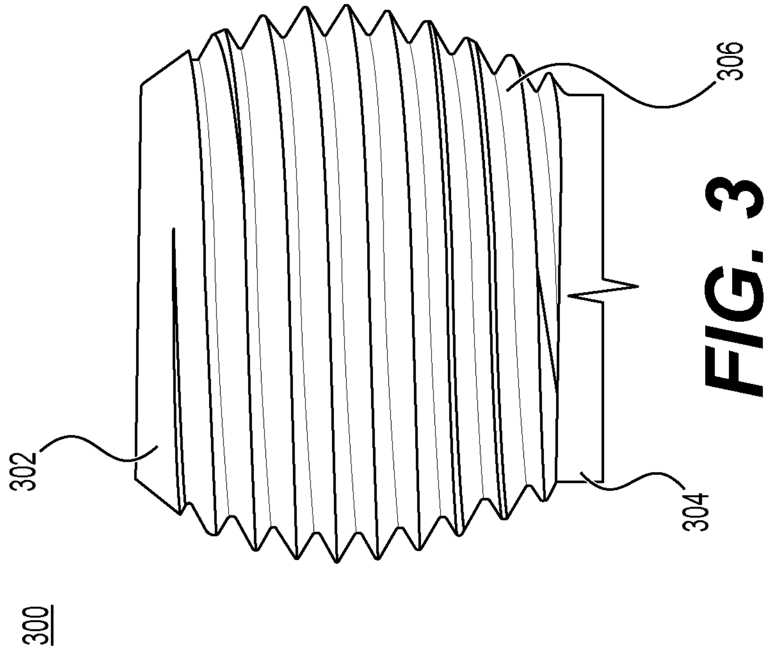
FIGS. 2 and 3 illustrate exemplary locking fasteners consistent with the principles of the present disclosure.
Figure 2:
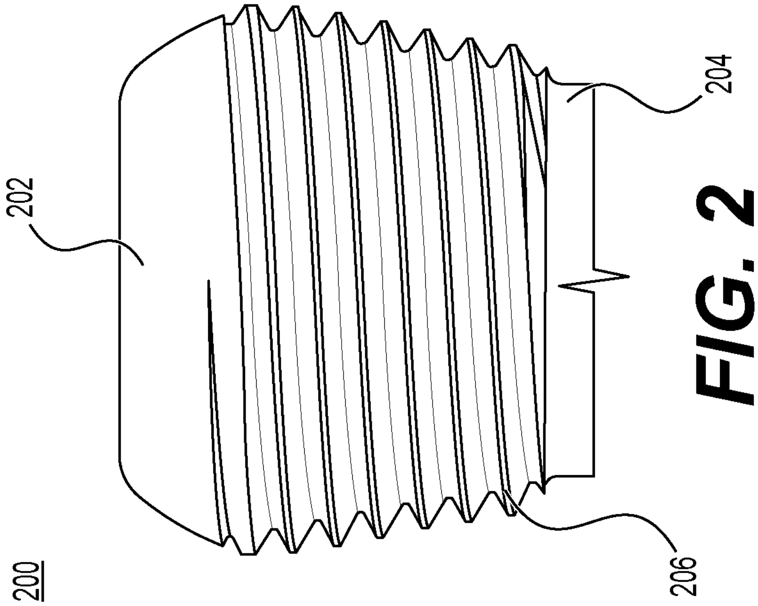

Specifically, locking fastener 200 of FIG. 2 may include a head portion 202 and a shaft portion 204 (shown in FIG. 6) configured to engage bone. Locking fastener 200 has a conical screw head profile with a textured area 206 with dual-lead threads. FIG. 3 illustrates a locking fastener 300 that has a screw head 302 and textured area 306. Screw head 302 has a spherical head profile with dual-lead threads. Each of bone screws 200 and 300 may be used under the principles of this disclosure according to any specific needs of a medical procedure and the preferences of a surgeon performing the medical procedure.

Figure 4:
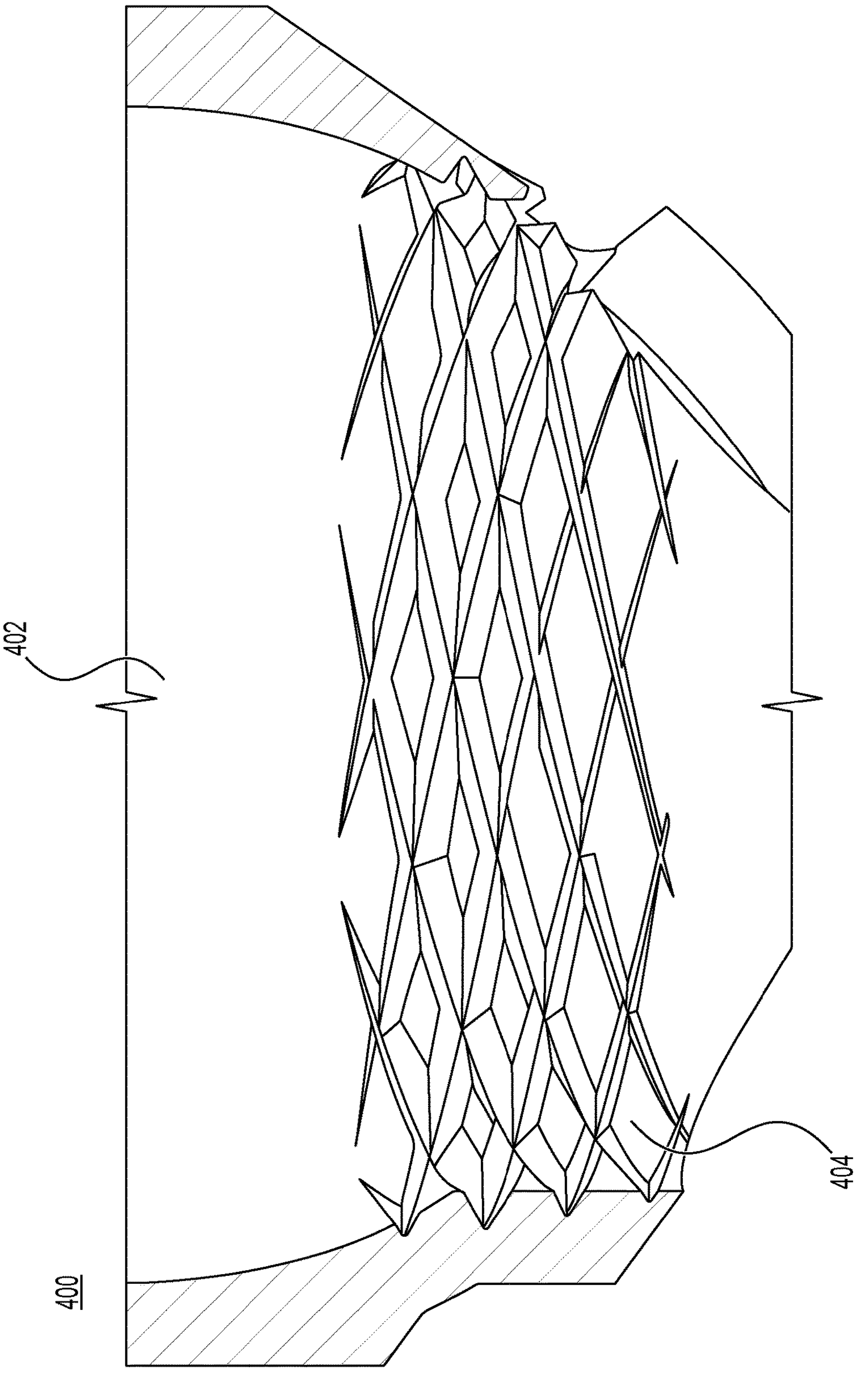
FIGS. 4 and 5 illustrate an exemplary bone plate consistent with the principles of the present disclosure.
Figure 5:
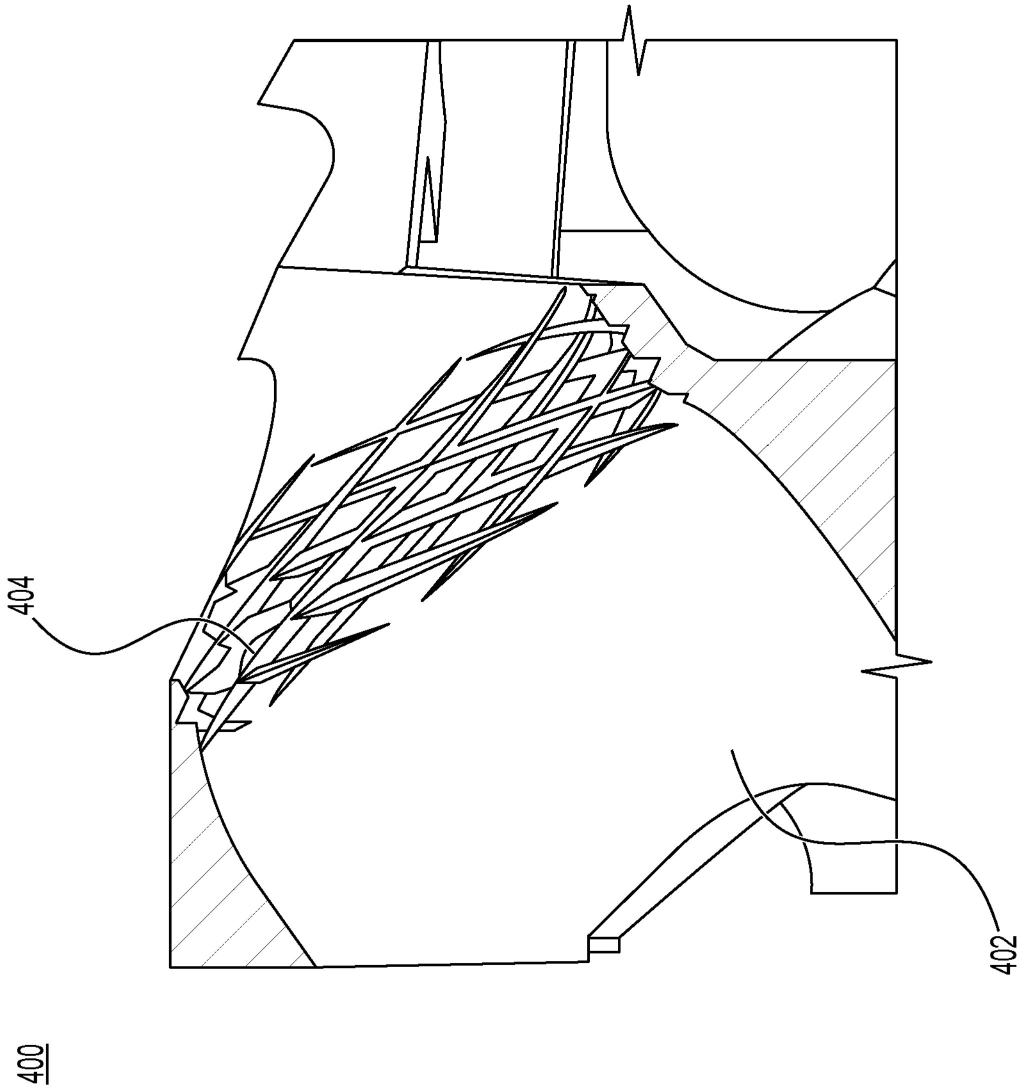

FIGS. 4 and 5 depict a plate 400 with a locking hole 402. An inside surface of screw hole 402 may be configured to have a textured portion 404, which may be, but not limited to, a series of helical sweeps, diamond knurls, threads, ridges, bumps, dimples, serrations or similar relief cuts arranged about the central axis of the screw hole or socket. The textured portion 404 may be of the same type (e.g., mating surfaces) or different from the textured area 206 of locking fastener 200. As shown, the textured portion 404 is disposed along an inner portion of the hole 402. The knurled surface may include straight, angled, or crossed lines cut or rolled into the material. For example, the textured portion 404 may take up about half or less of the surface area of hole 402.

An upper portion of the hole 402 may be tapered, without texturing, for example, to facilitate alignment of the fastener 200 with an opening of the locking hole 402. Locking hole 402 may be configured to receive a fixed or variable angle fastener 200. Locking hole 402 may be generally conical in shape such that it is wider near the top surface of plate 400 and narrower toward a bottom surface plate 400. The tapered portion and/or the textured portion 404 may be conical in shape.

Figure 6:
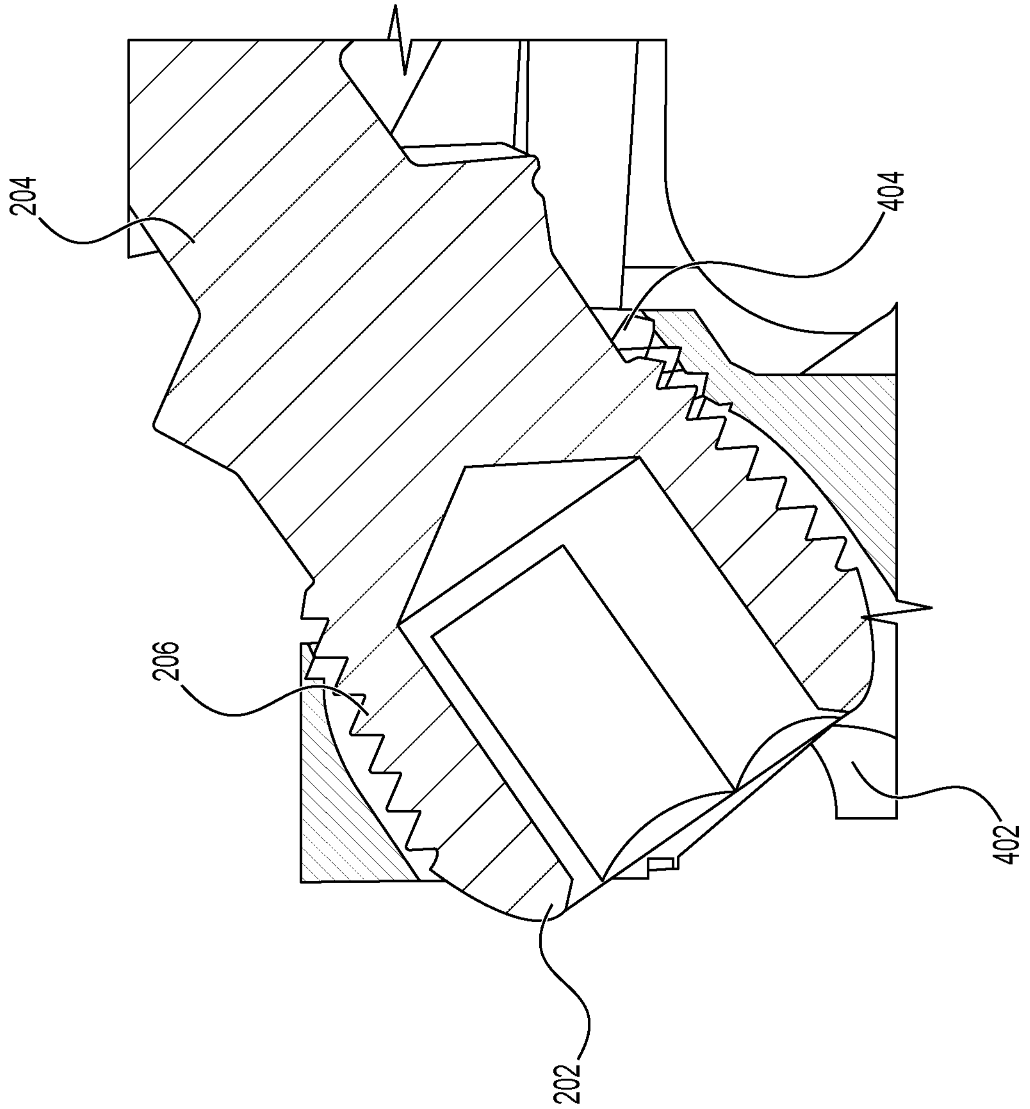
FIGS. 6 and 7 illustrate exemplary bone plates and locking fasteners consistent with the principles of the present disclosure.
Figure 7:
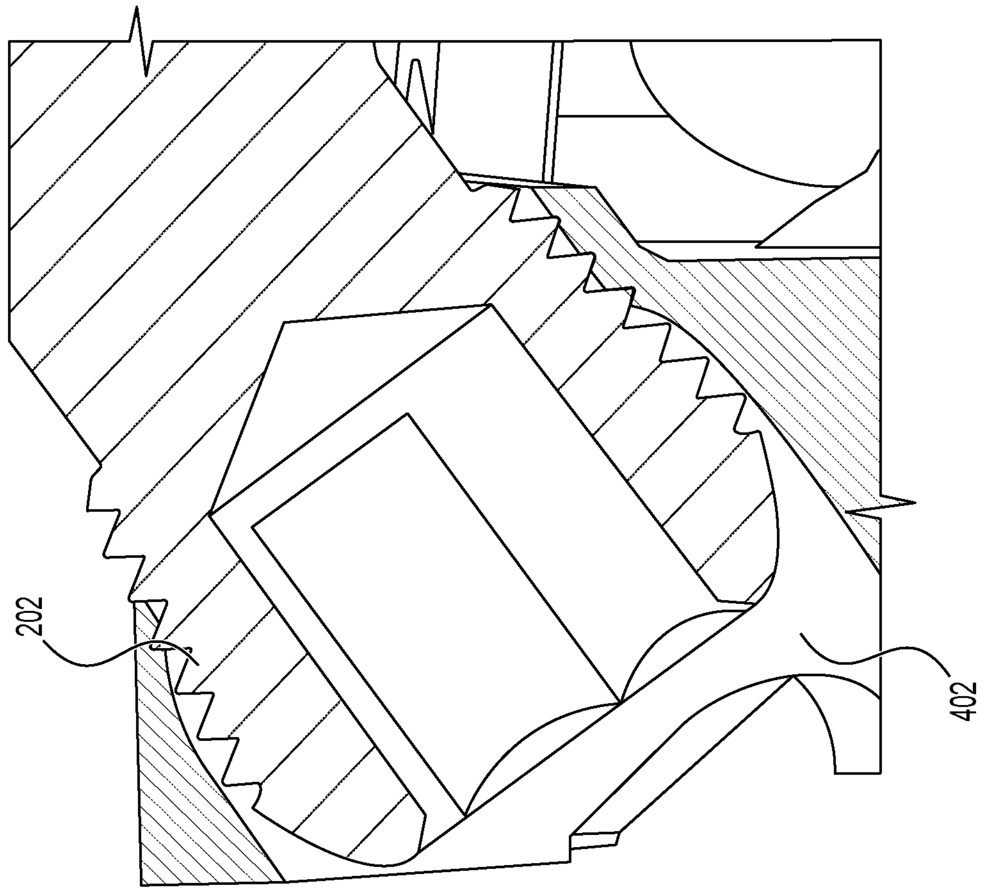

In operation, shaft portion 204 may be threaded such that the fastener 200 may be threaded into the bone. The head portion 202 of the locking fastener 200 may include the textured area 206 around its outer surface that is sized and configured to engage with locking hole 402 of plate 400. Textured area 206 may include threads, ridges, bumps, dimples, serrations, or other types of textured areas. As shown, texture area 206 preferably includes a threaded portion extending substantially from the top of the head portion 202 to the bottom of the head portion 202 proximate to the shaft portion 204. The textured portion 404 of locking holes 402 may deform as head 202 interferes with the textured portion 404 of the hole 402, thereby providing a positive lock between the fastener 200 and the plate 400. Thus, as shown in FIG. 6, when locking fastener 200 is engaged with plate 400, textured area 206 is screwed into textured area 404 thereby deforming textured area 404 to lock fastener 200 into plate 400.

In an alternate embodiment, locking hole 402 may be configured to have a substantially smooth surface rather than having textured surface 404. In this embodiment, when locking fastener 200 is inserted into plate 400, textured area 206 digs into the substantially smooth inner surface of the locking hole 402 thereby locking fastener 200 into plate 400.

Figure 9:
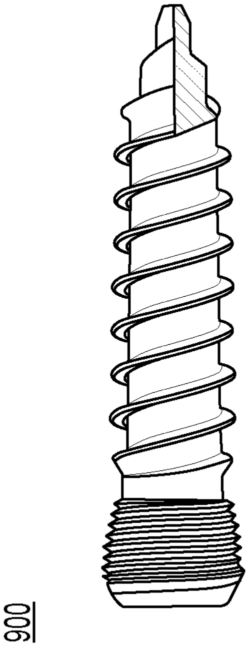
FIGS. 8-10 illustrates exemplary locking mechanisms consistent with the principles of the present disclosure.
Figure 10:
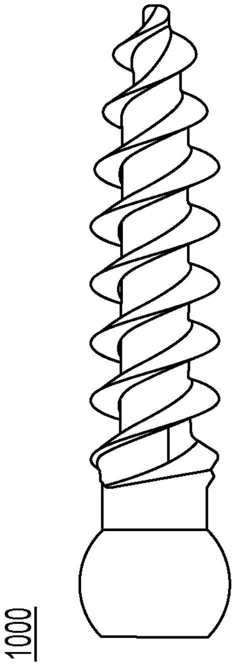
Figure 8:
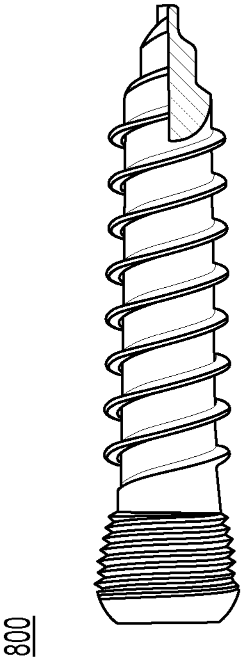

FIGS. 8-10 depict embodiments of bone screws 800, 900, and 1000 that may be used according to the principles of the present disclosure. Bone screws 800, 900, and 1000 maybe a fixed or variable angle 5.5 mm outside diameter (O.D.) screw. The screws may be spherically or conically tapered dual lead threads intended to create a rigid connection with a smooth screw hole or screw hole modified with helical sweeps, diamond knurls, or similar relief cuts. The tapering dual-lead threads may be configured to lock into a plate or integrated plate-spacer to provide a rigid stable construct in weak or osteoporotic bone. Additionally, the screw minor diameter and pitch may be modified to improve purchase in weak bone. The screw material may be TAV or cobalt-chromium (CoCr). A blocking screw may also be used to promote screw retention and further minimize the chance of back-out.

FIG. 8 depicts a fastener 800 that is a spherical head with a conical taper of the dual leads. FIG. 9 depicts a fastener 900 that is a spherical head with spherical thread taper variant. FIG. 10 depicts a non-locking, non-self-drilling variant with smaller minor diameter than that of fasteners 800 and 900.

The locking screw feature described above combined with large cancellous threads of the screw may allow for a rigid connection of the screw to the implant in cases where weakened bone prevents lagging of bone onto the implant surface. The screw-implant construct provides greater stability in patients with poor bone quality.

The cutting/wedging behavior of the conical threads allows for the use of a locking-type screw in the same socket or screw hole geometry as a non-locking lagging screw that uses a blocking screw feature for retention. This offers greater versatility the surgeon in the types of screws they can used for fixation depending on patient anatomy and bone quality while not altering existing lag screws.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all ranges broadly recited in this document include within their scope all narrower ranges which fall within the broader ranges. It is also intended that the components of the various devices disclosed above may be combined or modified in any suitable configuration.

What is claimed is:

1. A bone fixation system comprising:

a bone plate having an upper surface and a lower surface configured to be in contact with a bone, the bone plate having a locking hole with a textured portion; and a locking fastener, having a head portion and a shaft portion, configured to engage the textured portion and to be inserted into the bone, wherein the textured portion comprises diamond knurls arranged about a central axis of the locking hole, and the diamond knurls allow for both fixed and variable angle locking screws with conical variability up to 10 degrees.

2. The bone fixation system of claim 1, the bone plate having a locking hole that includes the textured portion and wherein the locking hole is generally conical in shape such that it is wider near the upper surface of the plate and narrower toward the lower surface of the plate.

3. The bone fixation system of claim 1, wherein the textured portion comprises a knurled surface.

4. The bone fixation system of claim 1, wherein the shaft portion comprises dual-lead threads for engagement with the bone.

5. The bone fixation system of claim 1, wherein the textured portion comprises a knurled surface including a pattern of straight, angled, or crossed lines cut into the plate.

6. The bone fixation system of claim 1, wherein the head portion is made of material that is harder than the textured portion.

7. The bone fixation system of claim 1, wherein the head portion is conical.

8. The bone fixation system of claim 1, wherein the head portion is spherical.

9. The bone fixation system of claim 1, further comprising a blocking screw configured to cover a portion of the locking fastener in a locked position to prevent the fastener from backing out of the plate.

10. A bone fixation system comprising:

a spacer configured to be inserted in between two adjacent vertebral bodies;

a bone plate having an upper surface and a lower surface configured to be in contact with a bone, the bone plate having a textured portion; and a locking fastener, having a head portion and a shaft portion, configured to configured to engage the textured portion and to be inserted into the bone, wherein the textured portion comprises diamond knurls arranged about a central axis of a locking hole, and the diamond knurls allow for both fixed and variable angle locking screws with conical variability up to 10 degrees.

11. The bone fixation system of claim 10, the bone plate having a locking hole that includes the textured portion and wherein the locking hole is generally conical in shape such that it is wider near the upper surface of the plate and narrower toward the lower surface of the plate.

12. The bone fixation system of claim 10, wherein the textured portion comprises a knurled surface arranged about a central axis of the locking hole.

13. The bone fixation system of claim 10, wherein the shaft comprises dual-lead threads for engagement with the bone.

14. The bone fixation system of claim 10, wherein the textured portion comprises a knurled surface including a pattern of straight, angled, or crossed lines cut into the plate.

15. The bone fixation system of claim 10, wherein the threaded head portion is made of material that is harder than the textured portion.

16. The bone fixation system of claim 10, wherein the head portion is conical.

17. The bone fixation system of claim 10, wherein the head portion is spherical.

18. The bone fixation system of claim 10, further comprising a blocking screw configured to cover a portion of the locking fastener in a locked position to prevent the fastener from backing out of the plate.

* * * * *